United States Patent [19]

Takase et al.

[11] Patent Number: 4,565,813
[45] Date of Patent: Jan. 21, 1986

[54] 1,4-THIAZINE DERIVATIVES
[75] Inventors: Muneaki Takase, Oizumi; Kimitomo Yoshioka, Tokyo; Hiroaki Yamazaki, Fujishiro, all of Japan
[73] Assignee: Zenyaku Kogyo Kabushiki Kaisha, Tokyo, Japan
[21] Appl. No.: 650,530
[22] Filed: Sep. 14, 1984
[30] Foreign Application Priority Data
Sep. 16, 1983 [JP] Japan .................. 58-170862
[51] Int. Cl.$^4$ .................. C07D 401/04; A61K 31/54
[52] U.S. Cl. .................. 514/222; 544/58.4
[58] Field of Search .................. 544/58.4; 514/222
[56] References Cited
U.S. PATENT DOCUMENTS
4,476,311 10/1984 Shetty et al. .................. 544/58.4

Primary Examiner—John M. Ford
Attorney, Agent, or Firm—Scrivener Clarke Scrivener and Johnson

[57] ABSTRACT

Disclosed is a novel 1,4-thiazine derivatives represented by the following general formula I and a pharmaceutically acceptable acid addition salt thereof:

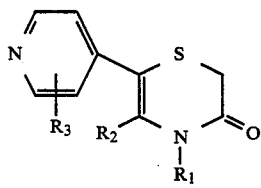

I wherein $R_1$, $R_2$ and $R_3$ respectively represent a hydrogen atom or a lower alkyl group. Also disclosed are processes for preparation of a novel thiazine derivative represented by the general formula I, which comprise reacting a compound of the general formula III with a compound of the general formula A-X' in a compound containing a pyridinyl group as a solvent to obtain a compound of the general formula II:

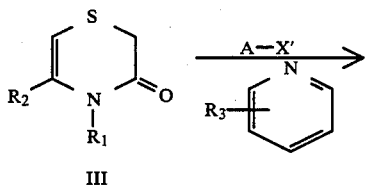

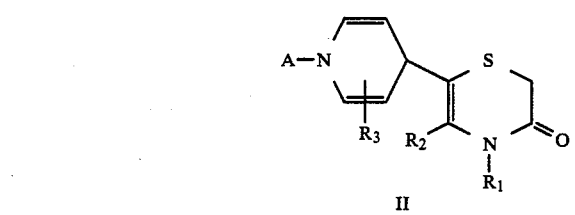

wherein $R_1$, $R_2$ and $R_3$ are as defined above, A represents a group

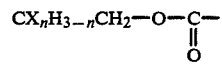

in which X represents a halogen atom and n is a number of 1 to 3, and X' represents a halogen atom which may be the same as or different from X, and reacting the compound of the general formula II with sulfur at elevated temperature or stirring the compound of the general formula II in a solution system comprising zinc and a carboxylic acid. Further disclosed is a cardiotonic agent comprising a pharmaceutically acceptable excipient and, as the active component thereof, an effective amount of the novel 1,4-thiazine derivative having the general formula I.

7 Claims, No Drawings

1,4-THIAZINE DERIVATIVES

BACKGROUND OF THE INVENTION

The present invention relates to a novel 1,4-thiazine derivative represented by the general formula I and a pharmaceutically acceptable acid addition salt thereof, and processes for preparation thereof and a cardiotonic agent comprising said novel 1,4-thiazine derivative as an effective component:

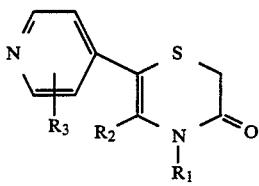

wherein $R_1$, $R_2$ and $R_3$ respectively represent a hydrogen atom or a lower alkyl group.

Known processes for the synthesis of thiazine derivatives include a process starting with a thioglycol amide derivative as disclosed in Journal of the American Chemical Society, 70, 3517 (1948), a process starting with a tricyclic compound as disclosed in Japanese Patent Publication No. 16630/1967, and a process starting with a thiazolium compound as disclosed in Japanese Patent Publication No. 29182/1970. However, such technique cannot apply to the synthesis of 1,4-thiazine derivatives having a pyridinyl group at position 6.

Many pyridone derivatives and pyridazinone derivatives are known which possess pharmaceutical properties affecting the cardiovascular system. These are described in Japanese Patent Provisional Publication No. 48675/1977, Journal of Medicinal Chemistry, 17, 273 (1974) and Japanese Patent Provisional Publication No. 109771/1982 and so on. However, there is no teaching in the prior art of any cardiotonically active compounds having any chemical structure comparable to or suggestive of an instantly claimed compound.

SUMMARY OF THE INVENTION

As the result of researches, we, the inventors succeeded in synthesizing a novel thiazine derivative having a cardiotonic effect and completed the present invention. According to the present invention, we provide a novel thiazine derivative having a pyridinyl group at position 6 and processes for preparation thereof, and a cardiotonic agent comprising said 1,4-thiazine derivative as an effective component.

DETAILED DESCRIPTION

The novel 1,4-thiazine derivative of the general formula I is prepared according to the following process.

When a known 1,4-thiazine derivative of the general formula III is reacted with a known compound of the general formula A-X' (in which A represents a group

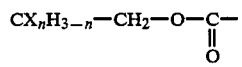

in which X represents a halogen atom and n is a number of 1 to 3, and X' represents a halogen atom which may be the same as or different from X) in a known solvent having a pyridinyl group such as pyridine, β-picoline or α-picoline, a novel 1,4-thiazine derivative of the general formula II is obtained:

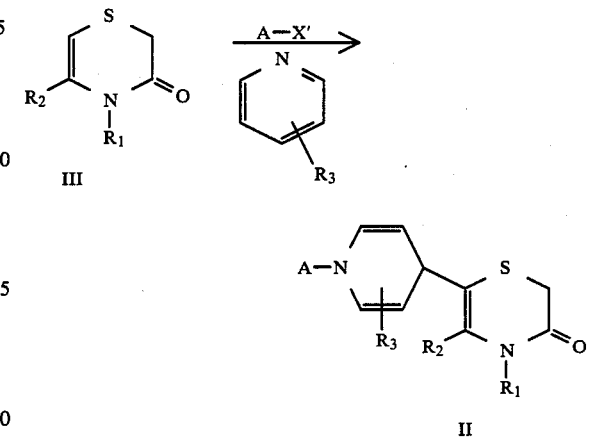

wherein $R_1$, $R_2$, $R_3$, A and X' are as defined above.

This reaction is completed by stirring substantially equimolar amounts of the compound of the general formula III and the compound of the general formula A-X' in the solvent having the pyridinyl group under atmospheric pressure and ambient temperature for more than 30 minutes, preferably 2–3 hours.

When the compound of the general formula II is reacted with sulfur at elevated temperaure, the intended novel 1,4-thiazine derivative of the general formula I is obtained.

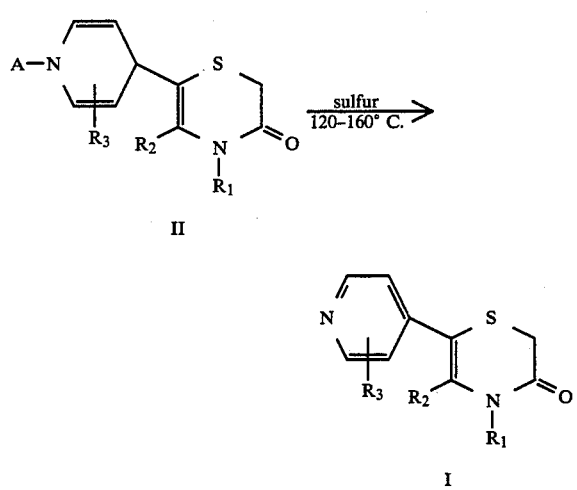

wherein $R_1$, $R_2$, $R_3$ and A are as defined above.

This reaction well proceeds by kneading the compound of the general formula II with about 5 fold amount sulfur and heating the mixture at 120° to 160° C. for 0.5 to 8 hours, preferably at about 140° C. for 1 hour. Generally, no solvent is needed in this reaction; however, N-N-dimethylformamide may be employed.

Purification of the compounds of the general formulae I and II can be accomplished by recrystallization from lower alcohols such as methanol, ethanol or isopropanol, ketones such as acetone, halogenated hydrocarbons such as chloroform or carboxylic acid esters such as ethyl acetate. It can be also be accomplished by development of silica gel column chromatography or silica gel thin layer chromatography. In this operation, silica gel having particles size of 100–200 mesh, such as Wakogel C-200 (manufactured by Wakojunyaku Kabushiki Kaisha in Japan) or silica gel having particles and average porous diameter of 60A and fluoresces a light blue color in the region of 254 nm such as Merck TLC plate silica gel 60F$_{254}$ (manufactured by Merck & Co. Inc. in USA) is preferable to use. Incidentally, the compound of the general formula II may be directly used in the subsequent reaction without purification.

The known starting material, 1,4-thiazine derivative of the general formula III can be prepared according to the following process.

In the case where $R_1$ in the general formula III is a hydrogen atom, the thiazine derivative of the general formula III is prepared according to processes proposed by H. Sokol et al. in J. Am. Chem. Soc., 70, 3517 (1948), C. R. Johnson et al. in J. Heterocycl. Chem., 6, 247–249 (1969), and G. V. Rao et al. in Synthesis, 136 (1972).

The thiazine derivative of the general formula III in which $R_1$ is a lower alkyl group may be prepared according to processes proposed by G. D. Stevens in J. Am. Chem. Soc., 80, 5198 (1958) and M. Hojo et al. in Synthesis, 272 (1979).

In view of the state of the reaction system (the reactivity and degree of dissociation) and the easy availability, an especially preferred compound of the general formula A-X' is one in which X and X' respectively represent a chlorine atom and n is 3, i.e. 2,2,2-trichloroethyl chloroformate.

The compound of the general formula I can also be prepared according to a process comprising stirring the compound of the general formula II in a solution system comprising an excessive amount of zinc and a carboxylic acid such as formic or acetic acid under atmospheric pressure and ambient temperature for more than 30 minutes, preferably 2–3 hours. According to this process, a novel 1,4-thiazine derivative having a piperidinyl group as a substituent at position 6 is formed as a by-product. Therefore, separation is necessary in this process. This process is represented by the following reaction formula:

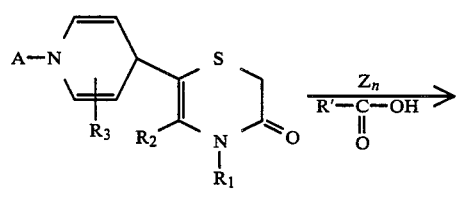

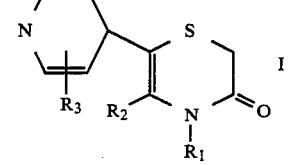

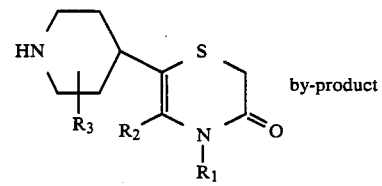

wherein $R_1$, $R_2$, $R_3$ and A are as defined above, and R' represents a hydrogen atom or a lower alkyl group.

Formic acid is preferred as the carboxylic acid used for this reaction. The 1,4-thiazine derivative having a piperidinyl group as a substituent at position 6, which is formed as a by-product in the above reaction, has also weak cardiotonic activity.

The compound of the general formula I may be converted into a pharmaceutically acceptable salt by using an appropriate acid.

The appropriate acids which can be used include, for example, inorganic acids such as hydrochloric, hydrobromic, sulfuric, nitric or phosphoric acid, and organic acids such as acetic, propionic, glycolic, lactic, pyruvic, malonic, succinic, maleic, fumaric, malic, tartaric, citric, benzoic, cinnamic, mandelic, methanesulfonic, hydroxyethanesulfonic, benzenesulfonic, p-toluenesulfonic, cyclohexanesulfamic, salicylic, p-aminosalicylic, 2-phenoxybenzoic or 2-acetoxybenzoic acid.

The pharmacological effects of the compound of the following general formula I will now be described:

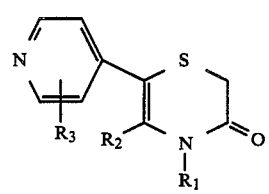

wherein $R_1$, $R_2$ and $R_3$ are as defined above.

(1) The contractile force of isolated atria was tested according to the method of L. J. Macleod described in Pharmacological Experiments on Intact Preparations, pages 112–115 (1970). A 7-weeks-old male Hartley guinea pig (having a body weight of about 350 g) was killed by a blow on the head. The chest was opened and the heart was removed as quickly as possible and placed in Ringer-Locke solution (prepared by adding distilled water to 9.0 g of sodium chloride, 0.25 g of potassium chloride, 0.15 g of calcium chloride and 1.0 g of glucose so that the total amount was 1,000 ml) at room temperature. All other tissues was cut away until nothing was left except the atria. Threads were tied to each tip of the atria and the preparation thus obtained was mounted in Ringer-Locke solution at 30±1° C., through which a brisk stream of pure oxygen was bubbled. One thread was attached to a fixed pin in the Magnus' bath and the other to a force-displacement transducer connected to an electrical amplifier and recorder. When the rate and amplitude became constant, recording was started. After 1 minute, the solution of sample compound was injected and recording was conducted for 2 minutes. After completion of recording, the isolated atria was washed with Ringer-Locke solution until the rate and amplitude became constant. After 15 minutes, recording was started again. The obtained results are shown in Table 1.

TABLE 1

Effect on Contractile Force of Isolated Atria

| Sample Compound | | | | Corresponding Concentration ($\mu$g/ml) | Maximum Contractile Force |
|---|---|---|---|---|---|
| Compound of general formula I according to present invention | $R_1 = H$ | $R_2 = CH_3$ | $R_3 = H$ | 50.0 | 40% increase |
| | $R_1 = CH_3$ | $R_3 = CH_3$ | $R_3 = H$ | 50.0 | 18% increase |
| By-product (general formula I) | $R_1 = H$ | $R_2 = CH_3$ | 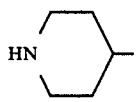 at position 6 | 50.0 | 5% increase |
| Control (isoproterenol) | | | | 50.0 | 40% increase |

From the above test results, it was confirmed that the contractile force of isolated atria was significantly increased by administration of the compound of the general formula I. It was also confirmed this activity of the compound of the general formula I is comparable to isoproterenol.

(2) The contractile force of isolated papillary muscles was tested according to the method described in Basic Lectures of Medicine Development, Volume V, Pharmacological Test Methods, Part 2, page 535 (1971). A female cat (having a body weight of about 3.5 kg) was anaesthetized with ether-chloroform gas and exsanguinated. The chest of each cat was opened and the heart was excised, rinsed with Krebs-Henseleit solution (prepared by adding distilled water to 6.92 g of sodium chloride, 0.35 g of calcium chloride, 0.29 g of magnesium sulfate, 0.16 g of mono-basic potassium phosphate, 2.1 g of sodium bicarbonate and 1.8 g of glucose so that the total amount was 1 l) and one or more small, thin papillary muscles from the right ventricule were dissected. Then papillary muscles were mounted in 20 ml Magnus' bath containing Krebs-Henseleit solution bubbled with oxygen gas at a temperature of 30±1° C. The papillary muscles were stimulated electrically at the rate of 2 beat/sec. and a voltage of 20% above threshold. The developed tension of the muscles was recorded isometrically on recorder by the use of force displacement tansducers. The results are shown in Table 2.

TABLE 2

Contractile Force of Isolated Papillary Muscles

| Sample Compound | Concentration (g/ml) | Maximum Contractile Force |
|---|---|---|
| Compound of general formula I according to present invention ($R_1 = H$, $R_2 = CH_3$, $R_3 = H$) | $1.0 \times 10^{-6}$ | 27% increase |
| | $1.0 \times 10^{-5}$ | 61% increase |
| Control (amrinone) | $1.0 \times 10^{-5}$ | 17% increase |
| | $1.0 \times 10^{-4}$ | 77% increase |

From the above test results, it was confirmed that the contractile force of isolated papillary muscles was significantly increased by administration of the compound of the general formula I. It was also confirmed that this activity of the compound of the general formula I is more than amrinone.

(3) The coronary-vasodilating effect was tested according to the method disclosed in Basic Lectures of Medicine Development, Volume V, Pharmacological Test Methods, Part 2, page 537 (1971). A 7-weeks-old male Hartley guinea pig (having a body weight of about 350 g) was used. And the measurement was carried out under a perfusion pressure of about 60 mmHg according to the Langendorff's method by using as a nutrient solution a Krebs' solution. The incubation temperature was 37° C. The obtained results are shown in Table 3.

TABLE 3

Coronary-Vasodilating Action

| Sample Compound | | | | Dose ($\mu$g) | Maximum Increase Ratio | 30 Minutes after Administration of Sample |
|---|---|---|---|---|---|---|
| Compound of general formula I according to present invention | $R_1 = H$ | $R_2 = CH_3$ | $R_3 = H$ | 500 | 71% | 10% |
| | $R_1 = CH_3$ | $R_2 = CH_3$ | $R_3 = H$ | 100 | 28% | 8% |
| By-product (general fomula I) | $R_1 = H$ | $R_2 = CH_3$ | 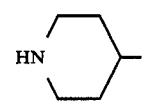 at position 6 | 500 | 12% | 5% |

TABLE 3-continued

| | | | Coronary Blood Flow Increase Ratio | |
|---|---|---|---|---|
| | Sample Compound | Dose (μg) | Maximum Increase Ratio | 30 Minutes after Administration of Sample |
| Control | Sodium nitrite | 500 | 20% | 5% |
| | Theophylline | 500 | 32% | −10% |

From the results shown above, it was confirmed that the administration of the compound of the general formula I is effective in increasing the coronary blood flow and this effect is continuous. It was found that the compound of general formula I has a coronary-vasodilating effect and the coronary blood flow increase ratio of the compound of the general formula I is higher than that of known sodium nitrite or theophylline having a coronary-vasodilating effect, and that the effect of the compound of the general formula I is continuous.

(4) The contractile force of ventricular muscle and heart rate in anaesthetized dog was tested according to the method described in Basic Lectures of Medicine Development, Volume V, Pharmacological Test Methods, Part 2, page 544 (1971). A male dog (having a body weight of about 12–14 kg) was anaesthetized with 40 mg/kg body weight of pentobarbital sodium (i.p.). Supplemental dose of pentobarbital was administered whenever necessary. An intra-tracheal cannula was inserted and ventilation was carried out by means of Harvard constant-volume, positive pressure pump using room air. The chest was opened by a midline incision and the heart was suspended in the pericardial cradle. The contratile force of the myocardium was measured by means of Walton-Brodie type strain-gauge arch sutured onto the left ventricle. Systemic blood pressure was measured from the left femoral artery by a pressure transducer and heart rate was calculated by blood pressure pulses. Sample compounds were infused into the left femoral vein at a rate of 320 μg/kg/minute until a maximum inotropic effect is obtained. The results are shown in Table 4.

TABLE 4

Contractile Force of Ventricular Muscle and Heart Rate of Anaesthetized Dog

| Sample Compound | Contractile Force of Ventricular Muscles | Heart Rate |
|---|---|---|
| Compound of general formula I according to present invention ($R_1$ = H, $R_2$ = $CH_3$, $R_3$ = H) | 170% increase | 30% up |
| Control (amrinone) | 25% increase | 25% up |

When tested by the above-described Anaesthetized Dog Procedure, the compound of the general formula I was found to cause significant increase of contractile force of ventricular muscle, with slight increase of heart rate. It was confirmed that this activity of compound of the general formula I is more than amrinone.

(5) The inhibition of platelet aggregation was determined according to the method of Yamazaki [Hiroo Yamazaki, Clinical Inspections, 22, (9) 935–943 (1978)]. Eleven-weeks-old male Wistar rats (having a body weight of about 350 g) were used. Blood was drawn by venupuncture in the antecubital fossa from normal donors. Nine fold volume of blood was drawn, with mixing, into a syringe containing one volume of 3.1% (W/V) sodium citrate. Platelet-rich-plasma (PRP) was collected as the supernatant after centrifuging the citrated blood at 1,000 rpm for 10 min. Platelet-poor-plasma (PPP) was the resulting supernatant after the residual citrated blood was additionally centrifuged at 3,000 rpm for 10 min. Each 210 μl aliquot of PPP and PRP was placed in cuvette and stirred at 37° C. in aggregometer. The aggregation reactions were determined by changes in light transmissions. A 20 μl sample was injected into PRP in the aggregometer, and 1–2 min. later, a 20 μl aggregation stimulant was injected. Aggregation pattern and maximal aggregation rate of each sample were compared with those of control. 100 μM of ADP (adenosine-5'-diphosphate or 100 μg/ml of collagen was used as the aggregation stimulant. The obtained results are shown in Table 5.

TABLE 5

Inhibition of Platelet Aggregation

| Sample Compound | | Corresponding Concentration (μg/ml) | Aggregation Inhibition Ratio | |
|---|---|---|---|---|
| | | | ADP | Collagen |
| Compound of general formula I according to present invention | $R_1$ = H $R_2$ = $CH_3$ $R_3$ = H | 83.0 | 80% | 100% |

It was confirmed that aggregation of the platelet can be inhibited by administration of the compound of the general formula I.

(6) Effect on systolic blood pressure and heart rate were tested according to the method disclosed in Basic Lectures of Medicine, Development, Volume V, Pharmacological Test Methods, Part 2, page 468 (1971). Male Wister rats (having a body weight of about 350 g) were used. Systolic blood pressure and heart rate were measured in rats by indirect tail-cuff method, using a programmed electrosphymomanometer. Systolic blood pressure and heart rate were measured at intervals of 1 hour and sample compounds were administrated with 25 mg/kg body weight (p.o.). The results are shown in Table 6.

TABLE 6

Effect on Systolic Blood Pressure and Heart Rate

| Sample Compound | Blood Pressure | Heart Rate |
|---|---|---|
| Compound of general formula I according to present invention ($R_1$ = H, $R_2$ = $CH_3$, $R_3$ = H) | decrease | 19% up |
| Control   Theophylline | increase | 29% up |
| Milrinone | decrease | 51% up |

From the above test results, it was confirmed that the blood pressure was decreased and the heart rate was increased by administration of the compound of the general formula I. It was also confirmed that the increase of heart rate is smaller than that of theophilline or milrinone.

(7) The bronchodilation effect was tested according to the method of L. J. Macleod in Pharmacological Experiments on Intact Preparations, Pages 100–103 (1970). A 7-weeks-old, male Hartley guinea pig (having a body weight of about 350 g) was killed by a blow on the head and cutting the throat. The trachea was dissected out and transferred into Krebs' solution. The excessive tissue was removed and the trachea was cut transversely with great care not to damage smooth muscle, to form at least 5 tracheal rings which are tied together so as to form chain. One thread was attached to a fixed pin in the Magnus' bath and the other, to a force-displacement transducer connected to an electrical amplifier and recorder. Experiments with this preparation were performed at $37\pm1°$ C. in Krebs' solution through which $O_2$ plus 5% $CO_2$ was bubbled. The sample compound was injected and the recording was conducted for 4 minutes. After completion of the recording, the sample was washed out with Krebs' solution until the base line became stable. After 30 to 50 minutes, the recording was started again. The obtained results are shown in Table 7.

TABLE 7

| Bronchodialation Effect | | |
|---|---|---|
| Sample Compound | | Influence of Smooth Muscle of Bronchus |
| Compound of general formula I according to present invention | $R_1 = H$<br>$R_2 = CH_3$<br>$R_3 = H$ | relaxed by 0.13 m/m or more |

It was confirmed that the smooth muscle of the bronchus is relaxed by administration of the compound of the general formula I. It was found that the compound of the general formula I has a bronchodilation effect.

From the results of the pharmacological tests (1) through (7), it has been confirmed that the compound of the general formula I has an excellent cardiotonic effect of a cyclic AMP-depending type. It has been found that the compound of the general formula I selectively increases the myocardium-contractile force without causing extreme increase of the heart rate.

The acute toxicity of the compound of the general formula I was determined according to the Litchfield-Wilcoxon method [J. Pharm. Exp. Ther., 96, 99 (1949)] using 6-weeks-old male ddY mice (having a body weight of 19 to 24 g) while administrating the sample compound in the tail vein. The obtained results are shown in Table 8.

TABLE 8

| Acute Toxicity Test Results | | |
|---|---|---|
| Sample Compound | | $LD_{50}$ (mg/kg) |
| Compound of general formula I according to present invention | $R_1 = H$<br>$R_2 = CH_3$<br>$R_3 = H$ | 165–200 |

As is apparent from the foregoing description, the novel 1,4-thiazine derivative of the present invention is a compound not described in any literature, and the 1,4-thiazine derivative of the present invention has a cardiotonic effect of a cyclic AMP-depending type and selectively increases the myocardium-contractile force without causing extreme increase of the heart rate. Furthermore, the acute toxicity of the 1,4-thiazine derivative of the present invention is low. Accordingly, the novel 1,4-thiazine derivative of the present invention is effective in curing and preventing heart diseases, especially cardiac insufficiency.

According to the process of the present invention, the novel 1,4-thiazine derivative of the present invention can be prepared from relatively easily available starting compounds in a high yield by a relatively easy operation. Accordingly, the process of the present invention is advantageous from the industrial viewpoint.

The present invention will now be described in detail with reference to the following examples.

In the examples the measurements were carried out by using the following apparatuses.

Melting point: Model MP-1 supplied by Yamato Kagaku Kabushiki Kaisha.

Elementary analysis: Model MT-2 supplied by Kabushiki Kaisha Yanagimoto Seisakusho.

Mass analysis: Maodl M-60 supplied by Kabushiki Kaisha Hitachi Seisakusho.

Infrared absorption (IR): Model 260-10 supplied by Kabushiki Kaisha Hitachi Seisakusho.

Nuclear Magnetic resonance (NMR): FX-270 supplied by Nippon Denshi Kabushiki Kaisha.

Magnus's bath: supplied by Kabushiki Kaisha Natsume Seisakusho.

Recorder: Model WI-680G supplied by Nippon Koden Kabushiki Kaisha.

Electrical amplifier: Model AP-600G supplied by Nippon Koden Kabushiki Kaisha.

Aggregometer: supplied by Niko Bioscience Kabushiki Kaisha.

Force displacement transducer: supplied by Nippon Koden Kabushiki Kaisha.

Programmed electrosphygmonometer: supplied by Nippon Koden Kabushiki Kaisha.

EXAMPLE 1

(1) Preparation of intermediate, 5-methyl-6-[1-(2,2,2-trichloroethoxycarbonyl)-1,4-dihydro-4-pyridinyl]-2H-1,4-thiazin-3(4H)-one.

To a solution of 5-methyl-2H-1,4-thiazin-3(4H)-one (1.5 g) in dry pyridine (20 ml), 2,2,2-trichloroethyl chloroformate (2.8 g) was added dropwise under ice bath temperature. The reaction mixture was stirred at room temperature for 3 hours. The solvent was removed under reduced pressure and the residue was extracted with chloroform. The extract was washed with 2N hydrochloric acid and water, and dried over anhydrous magnesium sulfate and chloroform was removed under reduced pressure. The residual oil was triturated with ether and recrystallized from ethanol using decolorizing chacoal to give 5-methyl-6-[1-(2,2,2-trichloroethoxycarbonyl)-1,4-dihydro-4-pyridinyl]-2H-1,4-thiazin-3(4H)-one (1.4 g, yield 31.5%) as light yellow scales.

Melting Point: 158°–160° C. Elementary analysis values as $C_{13}H_{13}O_3N_2SCl_3$: Calculated: C=40.69; H=3.41; N=7.29; (%) Found: C=40.62; H=3.37; N=7.02; (%).

Mass spectrum: M+382

NMR spectrum (CDCl$_3$, TMS, δ):

1.986 (3H, s), 3.229 (2H, s), 4.161 (1H, m), 4.800 (4H, m), 6.970 (2H, d), 7.264 (1H, b).

IR specturm $\gamma_{max}^{KBr}$ (cm$^{-1}$): 3200, 3100, 1720, 1670, 1630.

(2) Preparation of 5-methyl-6-(4-pyridinyl)-2H-1,4-thiazin-3(4H)-one.

(A) The mixture of 5-methyl-6-[1-(2,2,2-trichloroethoxycarbonyl)-1,4-dihydro-4-pyridinyl]-2H-1,4-thiazin3(4H)-one (2.14 g) and sulfur (10.7 g) was heated under stirring at 140° C. for 1.5 hours and then cooled to room temperature. The solid was extracted with methanol by using Soxhlet extractor. Methanol was removed under reduced pressure and the residue was dissolved in 50 ml of 2N hydrochloric acid. The insoluble solid was removed by filtration ad the filtrate was adjusted to pH 7.2 by 2N aqueous sodium hydroxide. The precipitates were collected by filtration and the filtrate was extracted with chloroform (20 ml×5 times) and evaporated to dryness. After combined with the above solid, the residue was recrystallized from isopropyl alcohol to give 5-methyl-6-(4-pyridinyl)-2H-1,4-thiazin-3(4H)-one (0.88 g, yield 76.5%) as light yellow plates.

Melting point: 187°–188.5° C. (decomposition) Elementary analysis values as: $C_{10}H_{10}N_2OS$: Calculated: C=58.22; H=4.88; N=13.58; (%) Found: C=58.48; H=4.99; N=13.53; (%).

Mass spectrum M+206

NMR spectrum (CDCl$_3$, TMS, δ): 2.056 (3H, s), 3.437 (2H, s), 7.280 (2H, d), 8.610 (2H, d), 8.700 (1H, s)

IR spectrum $\gamma_{max}^{KBr}$ (cm$^{-1}$): 3200, 3050, 1680, 1580.

(B) To a solution of 5-methyl-6-[1-(2,2,2-trichloroethoxycarbonyl)-1,4-dihydro-4-pyridinyl]-2H-1,4-thiazin-3(4H)-one (1 g) in formic acid (14 ml), zinc powder (1 g) was added and the reaction mixture was stirred at room temperature for 3 hours. The insoluble solid was removed by filtration. The filtrate was evaporated to dryness and the residue was dissolved in water (30 ml). The solution was adjusted to pH 7.0 by 1N aqueous sodium hydroxide. The precipitates were extracted with chloroform (although the solution was converted into an emulsion at this extracting step, the operation was facilitated by using a filter aid such as "Avicel"). The extract was dried over anhydrous magnesium sulfate and chloroform was removed under reduced pressure. The crude product was purified by the preparative thin layer chromatography [Merck TLC plate, silica gel 60F$_{254}$ (particles average porous diameter 60A, Fluorescent substance Zn$_2$SiO$_4$/Mn), 20×20 cm, t=1 mm, chloroform/methanol=20/1] to give 20 mg of 5-methyl-6-(4-pyridinyl)- 2H-1,4thiazin-3(4H)-one. The physical properties were as described above. The aqueous layer left after the chloroform extraction was adjusted to pH 12.5 by 1N aqueous sodium hydroxide and extracted with chloroform (50 ml×3 times). The extract was dried over anhydrous magnesium sulfate and chloroform was removed under reduced pressure. The residual solid was washed with ether and collected by filtration to give 5-methyl-6-(4-piperidinyl)-2H-1,4-thiazin-3(4H)-one (200 mg) as a light yellow powder.

Melting point: 180°–195° C. (decomposition) Elementary analysis values as $C_{10}H_{16}N_2OS$: Calculated: C=56.84; H=7.16; N=13.26; (%) Found: C=57.05; H=7.40; N=13.10; (%).

Mass spectrum: M+212

NMR spectrum (CDCl$_3$, TMS, δ): 1.65 (5H, m), 1.97 (3H, s), 2.60 (3H, m), 3.15 (4H, s+t), 8.25 (1H, s).

IR spectrum $\gamma_{max}^{KBr}$ (cm$^{-1}$): 3300, 3200, 3050, 1680, 1640.

(3) Preparation of 5-methyl-6-(4-pyridinyl)-2H-1,4-thiazin-3(4H)-one p-toluenesulfonate To a solution of 5-methyl-6-(4-pyridinyl)-2H-1,4-thiazin-3(4H)-one (0.88 g) in methanol (30 ml), p-toluenesulfonic acid monohydrate (0.97 g) was gradually added. The reaction mixture was stirred at room temperature for 30 minutes. Methanol was removed under reduced pressure and the residue was recrystallized from ethanol to give 5-methyl-6-(4-pyridinyl)-2H-1,4-thiazin-3(4H)-one p-toluenesulfonate (1 g, yield 62.5%) as yellow fine needles.

Melting point: 204°–206° C. (decomposition) Elementary analysis values as $C_{17}H_{18}N_2O_4S_2$: Calculated: C=53.94; H=4.79; N=7.40; (%) Found: C=53.70; H=4.86; N=7.16; (%).

NMR spectrum (DMSO-d$_6$, TMS, δ): 2.094 (3H, s), 2.291 (3H, s), 3.495 (2H, s), 7.120 (2H, d), 7.480 (2H, d), 7.955 (2H, d), 8.800 (2H, d), 10.383 (1H, s).

IR spectrum $\gamma_{max}^{KBr}$ (cm$^{-1}$): 3170, 3050, 1670, 1630(sh), 1580.

(4) Preparation of 5-methyl-6-(4-pyridinyl)-2H-1,4-thiazin-3(4H)-one hydrochloride To a solution of 5-methyl-6-(4-pyridinyl)-2H-1,4-thiazin-3(4H)-one (5 g) in methanol (500 ml), 12N hydrochloric acid (4 ml) was added dropwise with stirring at room temperature. The reaction mixture was stirred at room temperature for 1 hour and then concentrated in vacuo. Tetrahydrofuran (200 ml) was added and the reaction mixture was stirred at room temperature for 10 minutes, and then filtered. The residue was recrystallized from ethanol to give 4.6 g of 5-methyl-6-(4-pyridinyl)-2H-1,4-thiazin-3(4H)-one hydrochloride as pale yellow needles.

Melting point: more than 250° C. (decomposition)

(5) Preparation of 5-methyl-6-(4-pyridinyl)-2H-1,4-thiazin-3(4H)-one sulfate

5-Methyl-6-(4-pyridinyl)-2H-1,4thiazin-3(4H)-one (1 g) in methanol (100 ml) and 36N sulfuric acid (0.4 ml) were treated in the same manner as described in Example 1-(4) to give 0.95 g of 5-methyl-6-(4-pyridinyl)-2H-1,4-thiazin-3(4H)-one sulfate as yellow needles.

Melting point: 242°–243° C. (decomposition)

EXAMPLE 2

(1) Preparation of intermediate, 4,5-dimethyl-6-[1-(2,2,2-trichloroethoxycarbonyl)-1,4-dihydro-4-pyridinyl]-2H-1,4-thiazin-3-one In pyridine (8 ml) 4,5-dimethyl-2H-1,4-thiazin-3-one (0.42 g) and 2,2,2-trichloroethyl chloroformate (0.7 g) were treated in the same manner as described in Example 1-(1) to give 4,5-dimethyl-6-[1-(2,2,2-trichloroethoxy-carbonyl)-1,4-dihydro-4-pyridinyl]-2H-1,4-thiazin-3-one (0.38 g, yield 32.5%) as an oily product.

Mass spectrum: M+396

NMR spectrum (CDCl$_3$,TMS, δ): 2.096 (3H, s), 3.281 (3H, s), 3.405 (2H, s), 4.155 (1H, m), 4.800 (4H, m), 6.980 (2H, d)

IR spectrum $\gamma_{max}^{neat}$(cm$^{-1}$): 1720, 1690, 1660.

(2) Preparation of 4,5-dimethyl-6-(4-pyridinyl)-2H-1,4-thiazin-3-one

To a solution of 4,5-dimethyl-6-[1-(2,2,2-trichloroethoxycarbonyl)-1,4dihydro-4-pyridinyl]-2H-1,4-thiazin-3-one (0.38 g) in formic acid (5 ml), zinc powder (1.9 g) was added and the reaction mixture was stirred at room temperature for 2 hours. Zinc powder was removed by filtration and formic acid was removed under reduced pressure. The residue was dissolved in water and neutralized with 1N aqueous sodium hydroxide. The precipitates were extracted with ethyl acetate (50 ml×6 times). The combined extracts were dried over anhydrous magnesium sulfate and ethyl acetate was removed under reduced pressure to give an oily product. The oily product was purified by silica gel column chromatography (Wakogel C-200 particles size 100-200 mesh, chloroform/methanol=20/1) to give 4,5-dimethyl-6-(4-pyridinyl)-2H-1,4-thiazin-3-one (30 mg, yield 14.3%) as a light yellow powder.

Melting point: 139°-140° C. Elementary analysis values as $C_{11}H_{12}N_2OS$: Calculated: C=59.98; H=5.49; N=12.72; (%) Found: C=59.70; H=5.35; N=12.40; (%).

(3) Preparation of 4,5-dimethyl-6-(4-pyridinyl)-2H-1,4-thiazin-3-one p-toluenesulfonate To a solution of 4,5-dimethyl-6-(4-pyridinyl)-2H-1,4-thiazin-3-one (30 mg) in methanol (2 ml), p-toluenesulfonic acid (31.1 mg) was added and the mixture was treated in the same manner as described in Example 1-(3) to give 4,5-dimethyl-6-(4-pyridinyl)-2H-1,4-thiazin-3-one p-toluenesulfonate (30 mg, yield 56.3%).

Melting point: 169°-170° C. Elementary analysis values as $C_{18}H_{20}N_2O_4S_2$: Calculated: C=57.73; H=4.85; N=7.48; (%) Found: C=57.20; H=4.91; N=7.35; (%).

EXAMPLE 3

(1) Preparation of intermediate, 5-methyl-6-[1-(2,2,2-trichloroethoxycarbonyl)-3-methyl-1,4-dihydro-4-pyridinyl]-2H-1,4-thiazin-3(4H)-one To a solution of 3-methylpyridine (0.72 mg) in dry acetonitrile (10 ml) 2,2,2-trichloroethyl chloroformate (2.04 g) was added dropwise with stirring at −10° C. After stirring for 5 minutes 0.5 g of 5-methyl-2H-1,4-thiazin-3(4H)-one was added. The reaction mixture was stirred at −10° C. for 30 minutes and was stirred at room temperature for 3 hours. Acetonitrile was removed under reduced pressure. The residue was extracted with chloroform and chloroform extract was washed with 2N hydrochloric acid and water and dried over anhydrous magnesium sulfate and chloroform was removed under reduced pressure. The residue was purified by silica gel column chromatography (Wakogel C-200, ethylacetate/n-hexane=1/1) to give 0.49 g of 5-methyl-6-[1-(2,2,2-trichloroethoxycarbonyl)-3-methyl-1,4-dihydro-4-pyridinyl]-2H-1,4-thiazin-3(4H)-one as milk-white needles.

Melting point: 149°-152° C.

NMR spectrum (CDCl$_3$, TMS, δ)
1.65 (3H, s), 2.03 (3H, s), 3.21 (2H, d), 4.02 (1H, d); 4.74-4.96 (3H, m), 6.80 (1H, d), 6.98 (1H, d), 8.04 (1H, s).

IR spectrum $\gamma_{max}^{KBr}$ (cm$^{-1}$): 3190, 3070, 2930, 1720, 1670, 1630, 1380, 1320.

(2) Preparation of 5-methyl-6-(3-methyl-4-pyridinyl)-2H-1,4-thiazin-3(4H)-one The mixture of 5-methyl-6-[1-(2,2,2-trichloroethoxycarbonyl)-3-methyl-1,4dihydro-4-pyridinyl]-2H-1,4-thiazin-3(4H)-one (250 mg) and sulfur (125 mg) in N,N-dimethylformamide (2 ml) was heated at 160° C. for 1 hour. N,N-dimethylformamide was removed under reduced pressure and residue was extracted with 2N hydrochloric acid. The insoluble solid was removed by filtration and filtrate was washed with ether. The aqueous solution was adjusted to pH 7.2 by 2N aqueous sodium hydroxide. The precipitates were extracted with chloroform and the extract was dried over anhydrous magnesium sulfate. Chloroform was removed under reduced pressure and residue was purified by silica gel column chromatography (Wakogel C-200, chloroform/methanol=20/1) to give 118 mg of 5-methyl-6-(3-methyl-4-pyridinyl)-2H-1,4-thiazin-3(4H)-one as pale-brown crystal.

Melting point: 185°-187° C.

NMR spectrum (CDCl$_3$, TMS, δ):
1.78 (3H, s), 2.31 (3H, s), 3.44 (2H, s), 7.09 (1H, d), 8.44 (1H, d), 8.51 (1H, s), 8.58 (1H, s).

IR spectrum $\gamma_{max}^{KBr}$ (cm$^{-1}$): 3040, 2850, 1670, 1630, 1590, 1330.

What is claimed is:

1. A 1,4thiazine derivative represented by the following formula I and a pharmaceutically acceptable acid addition salt thereof:

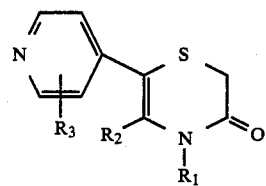

wherein $R_1, R_2$ and $R_3$ respectively represent a hydrogen atom or a lower alkyl group.

2. 5-Methyl-6-(4-pyridinyl)-2H-1,4-thiazin-3(4H)-one, according to claim 1.

3. A process for preparation of a thiazine derivative represented by the following formula I:

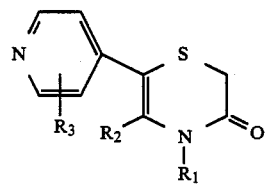

wherein $R_1$, $R_2$ and $R_3$ respectively represent a hydrogen atom or a lower alkyl group, which comprises reacting a compound of the formula III with a compound of the formula A-X' in a solvent having a pyridinyl group to obtain a compound of the formula II:

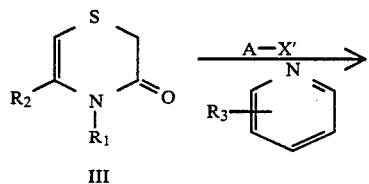
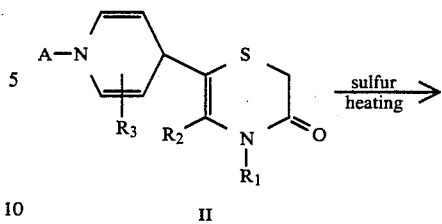

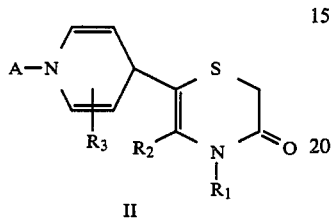

wherein $R_1$, $R_2$ and $R_3$ are as defined above, A represents a group

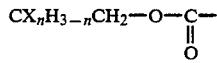

in which X represents a halogen atom and n is a number of 1 to 3, and X' represents a halogen atom which may be the same as or different from X, and reacting the compound of the formula II with sulfur at elevated temperature:

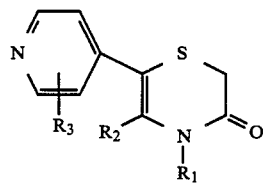

wherein $R_1$, $R_2$, $R_3$ and A as defined above.

4. A process according to claim 3 wherein the compound of the formula A-X' is 2,2,2-trichloroethoxy chloroformate.

5. A process according to claim 3 wherein the heating temperature is 120° to 160° C.

6. A cardiotonic agent comprising a pharmaceutically acceptable excipient and, as the active component thereof, an effective amount of a 1,4-thiazine derivative having the following formula I:

wherein $R_1$, $R_2$ and $R_3$ respectively represent a hydrogen atom or a lower alkyl group.

7. An agent according to claim 6 wherein the active component is 5-methyl-6-(4-pyridinyl)-2H-1,4-thiazin-3(4H)-one.

* * * * *